United States Patent
Ukawa

(10) Patent No.: US 8,744,542 B2
(45) Date of Patent: Jun. 3, 2014

(54) CARDIOPULMONARY RESUSCITATION MONITORING APPARATUS

(75) Inventor: Teiji Ukawa, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 139 days.

(21) Appl. No.: 13/416,226

(22) Filed: Mar. 9, 2012

(65) Prior Publication Data

US 2012/0245442 A1  Sep. 27, 2012

(30) Foreign Application Priority Data

Mar. 25, 2011 (JP) ................................. 2011-067217

(51) Int. Cl.
*A61B 5/1455* (2006.01)
*A61H 31/00* (2006.01)

(52) U.S. Cl.
USPC ............................................. 600/323; 601/41

(58) Field of Classification Search
USPC ...................... 600/310, 322, 323, 324; 601/41
See application file for complete search history.

(56) References Cited

U.S. PATENT DOCUMENTS 5,355,882 A    10/1994 Ukawa et al.
7,190,999 B2 *  3/2007 Geheb et al. .................... 601/41
7,569,018 B1    8/2009 Geddes et al.
2001/0047140 A1 * 11/2001 Freeman ........................ 601/41
2004/0267324 A1 12/2004 Geheb et al.
2004/0267325 A1 12/2004 Geheb et al.
2008/0171311 A1  7/2008 Centen et al.

FOREIGN PATENT DOCUMENTS

| EP | 0451560 A2 | 10/1991 |
| EP | 2497417 A1 | 9/2012 |
| JP | 3116252 B2 | 10/2000 |
| JP | 200546606 A | 2/2005 |

OTHER PUBLICATIONS

Extended European Search Report dated Jul. 19, 2012 issued in counterpart European Patent Application No. 12160252.8.
Office Action dated Jun. 12, 2013 issued by the European Patent Office in counterpart European Application No. 12160252.8.

\* cited by examiner

*Primary Examiner* — Eric Winakur
(74) *Attorney, Agent, or Firm* — Sughrue Mion, PLLC

(57) ABSTRACT

A cardiopulmonary resuscitation monitoring apparatus includes: a detecting unit configured to obtain a detection signal of a timing of chest compression during execution of cardiopulmonary resuscitation; a pulse oximeter configured to detect a change of a blood volume at the timing of the chest compression based on the detection signal, and configured to obtain an oxygen saturation from the change of the blood volume; an evaluating unit configured to perform evaluation related to the cardiopulmonary resuscitation based on the oxygen saturation; and an outputting unit configured to perform an outputting operation in accordance with a result of the evaluation.

4 Claims, 5 Drawing Sheets

CARDIOPULMONARY RESUSCITATION MONITORING APPARATUS

BACKGROUND OF THE INVENTION

The present invention relates to a cardiopulmonary resuscitation monitoring apparatus which performs monitoring in order to enable a rescuer or the like to perform an optimum cardiac massage maneuver when, for example, cardiopulmonary resuscitation is executed.

In order to determine the adequateness of cardiopulmonary resuscitation (CPR) by measuring lung inflation due to the cardiopulmonary resuscitation, a technique using the thoracic impedance is employed. In the lung inflation measurement using the thoracic impedance, however, it is impossible to determine whether blood oxygenation and the blood flow status are improved or not.

On the other hand, a technique using SpO2 in order to monitor blood oxygenation during execution of cardiopulmonary resuscitation is known (see JP-A-2005-46606). During execution of cardiopulmonary resuscitation, however, pulse waves which are effective in a measurement of SpO2 cannot be obtained, and therefore the measurement is sometimes disabled. Moreover, a body motion due to cardiopulmonary resuscitation produces disturbances, and it is difficult to correctly perform the measurement.

It is known that the DC component of transmitted light has information of blood oxygenation, and this is effective in correction of noise contamination (see Japanese Patent No. 3,116,252). However, Japanese Patent No. 3,116,252 discloses only correction corresponding to noise contamination which temporarily occurs in a measurement of SpO2. In Japanese Patent No. 3,116,252, a situation where SpO2 cannot be obtained because pulse waves do not exist in a state where cardiopulmonary resuscitation must be performed is not considered.

SUMMARY

It is therefore an object of the invention to provide a cardiopulmonary resuscitation monitoring apparatus which monitors effects of a cardiac massage maneuver that is performed by a rescuer or the like.

In order to achieve the object, according to the invention, there is provided a cardiopulmonary resuscitation monitoring apparatus comprising: a detecting unit configured to obtain a detection signal of a timing of chest compression during execution of cardiopulmonary resuscitation; a pulse oximeter configured to detect a change of a blood volume at the timing of the chest compression based on the detection signal, and configured to obtain an oxygen saturation from the change of the blood volume; an evaluating unit configured to perform evaluation related to the cardiopulmonary resuscitation based on the oxygen saturation; and an outputting unit configured to perform an outputting operation in accordance with a result of the evaluation.

The detecting unit may be configured by a displacement sensor, a speed sensor, an acceleration sensor, or a pressure sensor.

A light emitting section and a light receiving section of the pulse oximeter may constitute the detecting unit, and the detecting unit may be adapted to be placed on a surface of a living body.

DETAILED DESCRIPTION OF EMBODIMENTS

Figure 1:
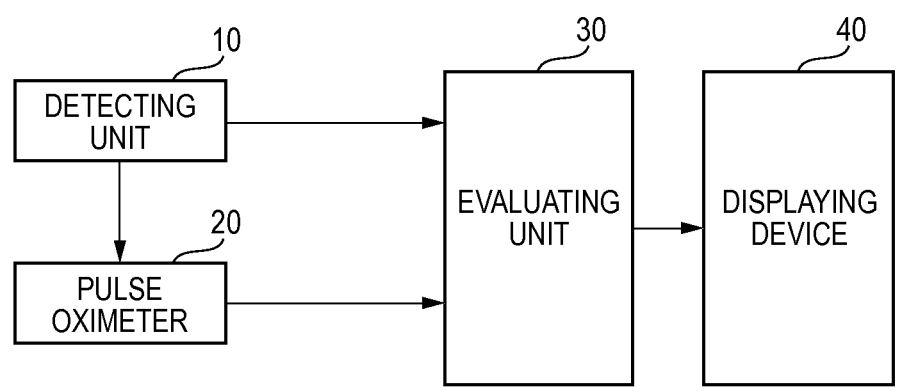
FIG. 1 is a block diagram showing the configuration of a first embodiment of the cardiopulmonary resuscitation monitoring apparatus of the invention.

Hereinafter, embodiments of the cardiopulmonary resuscitation monitoring apparatus of the invention will be described with reference to the accompanying drawings. In the figures, the identical components are denoted by the same reference numerals, and duplicated description will be omitted. FIG. 1 shows an embodiment of the cardiopulmonary resuscitation monitoring apparatus of the invention. The apparatus includes a detecting unit 10, a pulse oximeter 20, an evaluating unit 30, and a displaying device 40 which is an outputting unit.

The detecting unit 10 obtains a detection signal of a timing of chest compression during execution of cardiopulmonary resuscitation, and may be placed in a portion where chest compression is performed, and configured by a displacement sensor, a speed sensor, an acceleration sensor, or a pressure sensor. The pulse oximeter 20 detects a pulse wave to detect the oxygen saturation by using the pulse wave. For example, the configuration which is disclosed in Japanese Patent No. 3,116,252 above may be employed.

The pulse oximeter 20 detects the oxygen saturation by using the pulsation due to the pulse. Cardiopulmonary resuscitation is a life-saving measure which is artificially performed on a patient experiencing ventricular fibrillation or the like because such a patient has no pulse and the blood does not flow from the heart.

The evaluating unit 30 performs evaluation related to cardiopulmonary resuscitation based on the oxygen saturation which is obtained from a change of the blood volume pulse wave that is detected by the pulse oximeter 20 at the chest compression timing based on the detection signal obtained by the detecting unit 10. For example, the evaluating unit 30 may be configured by a computer. When the level (for example, the displacement level, the speed level, the acceleration level, or the pressure level) of the obtained signal exceeds a preset threshold, the detecting unit 10 deems this timing as the timing when each chest compression in execution of cardiopulmonary resuscitation is performed, and identifies the timing when the signal level exceeds the threshold, and notifies the timing to the pulse oximeter 20.

When this timing is referred to as the chest compression synchronization signal, for example, the pulse oximeter 20 can use variation of the received light intensity which is synchronized with the chest compression synchronization signal, as the blood flow variation due to the chest compression, in place of the pulse. Namely, the pulse oximeter 20 detects a change of the blood volume from an intensity change of the received light, and obtains the oxygen saturation. The evaluating unit 30 fetches the oxygen saturation signal SpO2 sent from the pulse oximeter 20, measures the trend of blood oxygenation from a change of the value, and evaluates whether a cardiac massage maneuver by a rescuer or the like is properly performed or not.

The evaluating unit 30 sends a result of the evaluation to the displaying device 40. The displaying device 40 performs an outputting operation in accordance with the result of the evaluation by the evaluating unit 30. In the above, the displaying device 40 which is an outputting unit may be a device that shows characters by means of a display such as an LCD, or a device which outputs a message simply by lighting, that which outputs a message by means of an audio output, or that which outputs a message by a necessary combination of these means. The displaying device 40 may be any kind of device as far as it can perform an output showing the evaluation by the evaluating unit 30.

Figure 2:
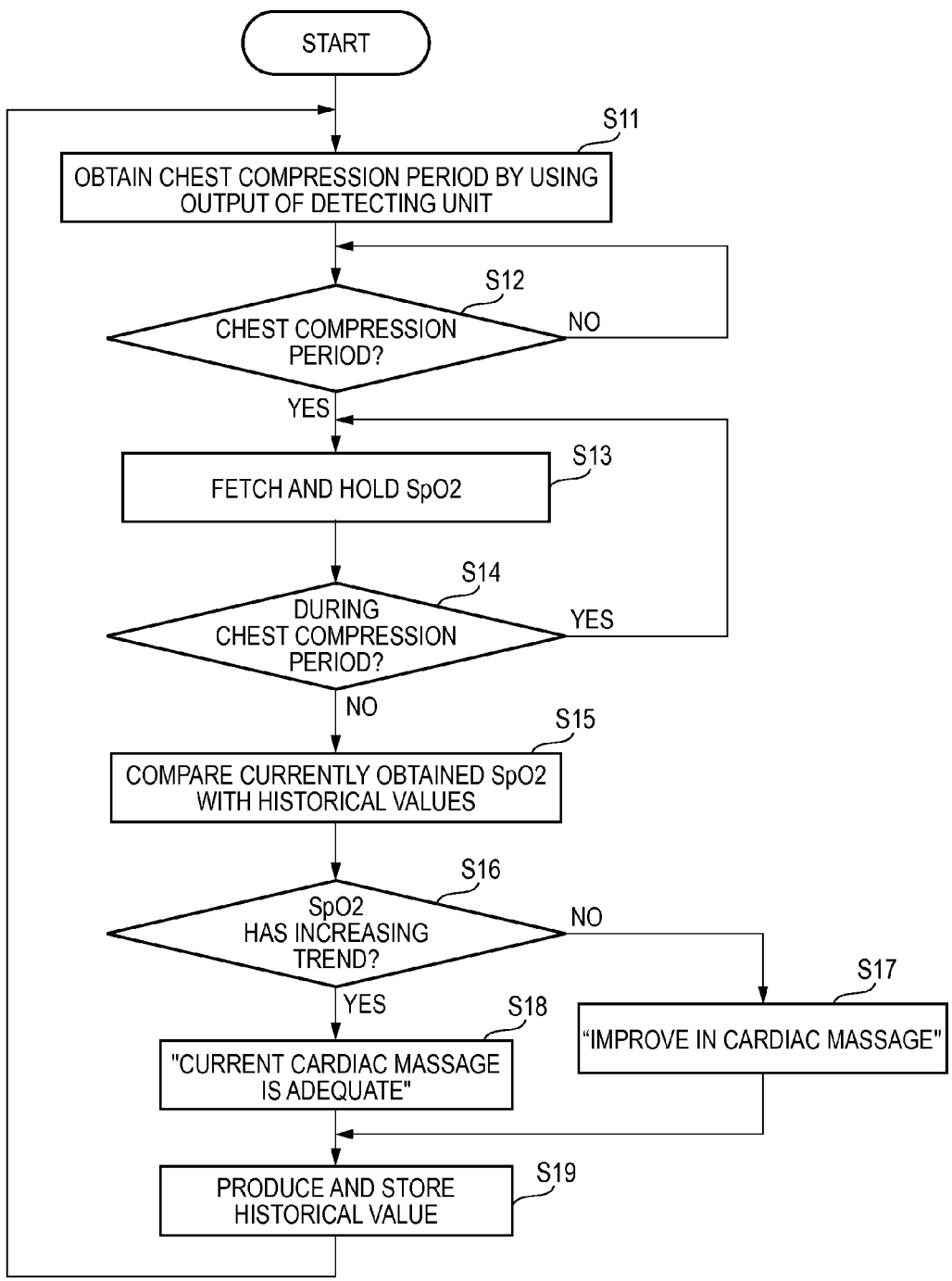
FIG. 2 is a flowchart illustrating the operation of the first embodiment of the cardiopulmonary resuscitation monitoring apparatus of the invention.

FIG. 2 is a flowchart showing the operation which is executed by the evaluating unit 30. The operation will be described with reference to the flowchart. First, the output of the detecting unit 10 is fetched, the process of obtaining a chest compression period during which chest compression is performed is conducted (S11), and it is detected whether the chest compression period is reached or not (S12).

If the chest compression period is reached, the oxygen saturation signal SpO2 which is the output of the pulse oximeter 20 is fetched and held (S13), it is detected whether the current timing is in the chest compression period or not (S14), and, if the current timing is in the chest compression period, the oxygen saturation signal SpO2 is kept to be fetched and held in synchronization with chest compression (S13). When the chest compression period is ended, the oxygen saturation signal SpO2 which is fetched and held is compared with past historical values (S15), and it is detected whether the blood oxygen saturation has an increasing trend or not (S16).

If it is determined in step S16 that the blood oxygen saturation does not have an increasing trend, message information of "Improve in cardiac massage" is sent to the displaying device 40 which is an outputting unit, to be displayed thereon (S17). If it is determined in step S16 that the blood oxygen saturation has an increasing trend, message information of "Current cardiac massage is adequate" is sent to the displaying device 40 which is an outputting unit, to be displayed thereon (S18). In succession to step S17 or S18, a historical value is produced by using the blood oxygen saturation, and stored (S19). Then, the process returns to step S11.

Figure 3:
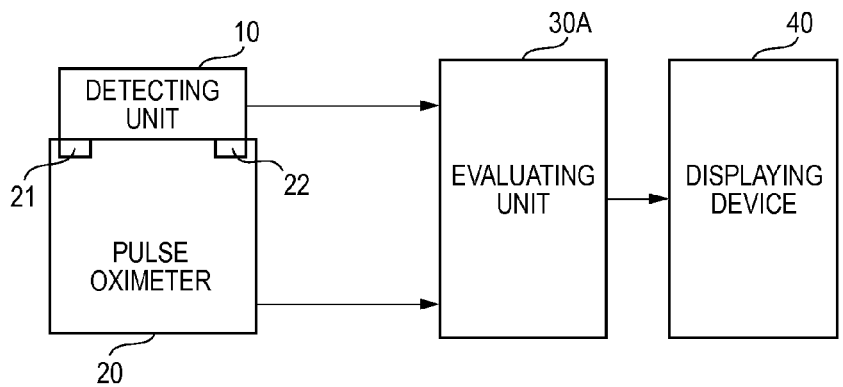
FIG. 3 is a block diagram showing the configuration of a second embodiment of the cardiopulmonary resuscitation monitoring apparatus of the invention.

FIG. 3 is a diagram showing the configuration of the cardiopulmonary resuscitation monitoring apparatus of a second embodiment. In the embodiment, light emitting and receiving sections 21, 22 of the pulse oximeter 20 are placed on the surface of the living body where the detecting unit 10 is placed. Alternatively, the light emitting and receiving sections 21, 22 and the detecting unit 10 may be disposed in one chassis. The other configuration is identical with that of the first embodiment. In the embodiment, it is not always necessary that the displacement sensor, speed sensor, acceleration sensor, or pressure sensor which has been described in the first embodiment is used as the detecting unit 10, because an intensity change of light received by the light receiving section 22 can be used as means for detecting chest compression.

One light which is emitted from the light emitting section 21 and incident on the living body is red light having a received light intensity Ri, and the other is infrared light having a received light intensity Ii. When these light are transmitted through the living body, red light having a transmitted light intensity Ro, and infrared light having a transmitted light intensity Io are obtained. The above description refers to the case in which chest compression is not performed, and which is shown in FIG. 4A.

Figure 4A:
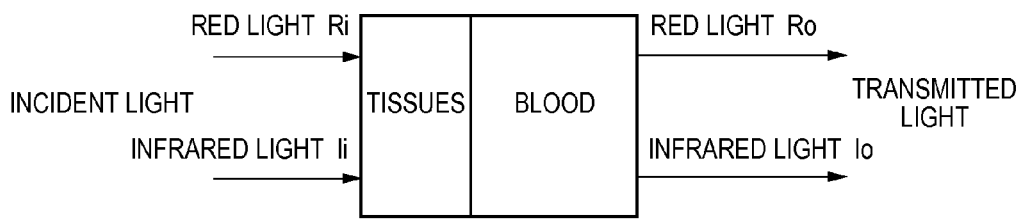
FIGS. 4A and 4B are views illustrating the state of a living body, incident light, and transmitted light before and after execution of cardiopulmonary resuscitation.
Figure 4B:
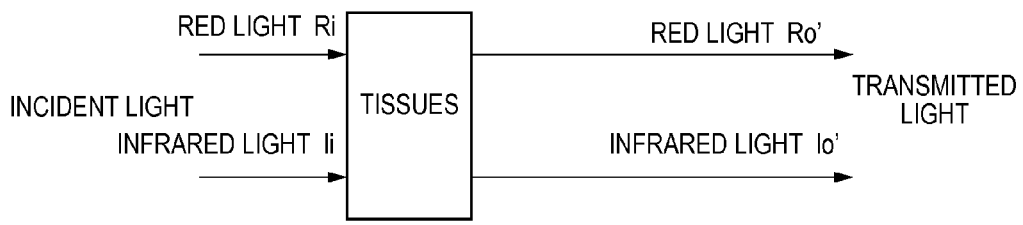

By contrast, if cardiopulmonary resuscitation is being executed and chest compression is performed, the blood layer is largely pressed, and the state of FIG. 4B where light is transmitted only through living body tissues is attained. At this time, red light having a received light intensity Ro' and infrared light having a received light intensity Io' are obtained. The red light having a received light intensity Ro' and the infrared light having a received light intensity Io' can be deemed as light incident on the blood layer, and measurement according to the principle of a pulse oximeter is enabled.

Referring to FIGS. 4A and 4B, the description has been made while assuming that transmission is performed. Actually, however, the pulse oximeter 20 performs the process based on reflected light because the light emitting and receiving sections 21, 22 are placed on the surface of the living body where the detecting unit 10 is placed.

By using the output of the detecting unit 10, an evaluating unit 30A obtains a timing when chest compression is performed. Unlike the first embodiment, the evaluating unit 30A is requested to detect not each chest compression but whether, for example, cardiopulmonary resuscitation is continued or not. When variation of the output of the displacement sensor or the pressure sensor is detected, for example, the evaluating unit 30A performs evaluation in which the oxygen saturation signal SpO2 sent from the pulse oximeter 20 is used, and, when the output variation is not produced for a constant time period, stops the evaluation process.

Figure 5:
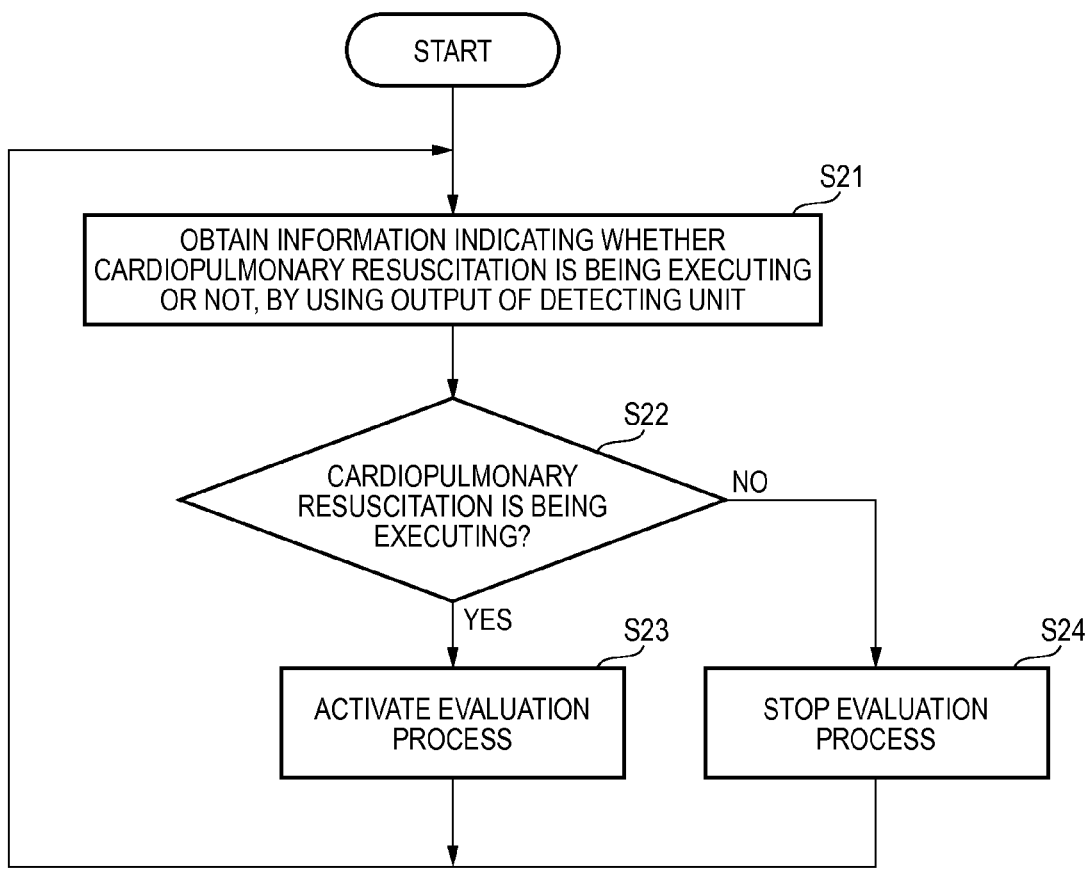
FIG. 5 is a flowchart illustrating the operation of the second embodiment of the cardiopulmonary resuscitation monitoring apparatus of the invention.
Figure 6:
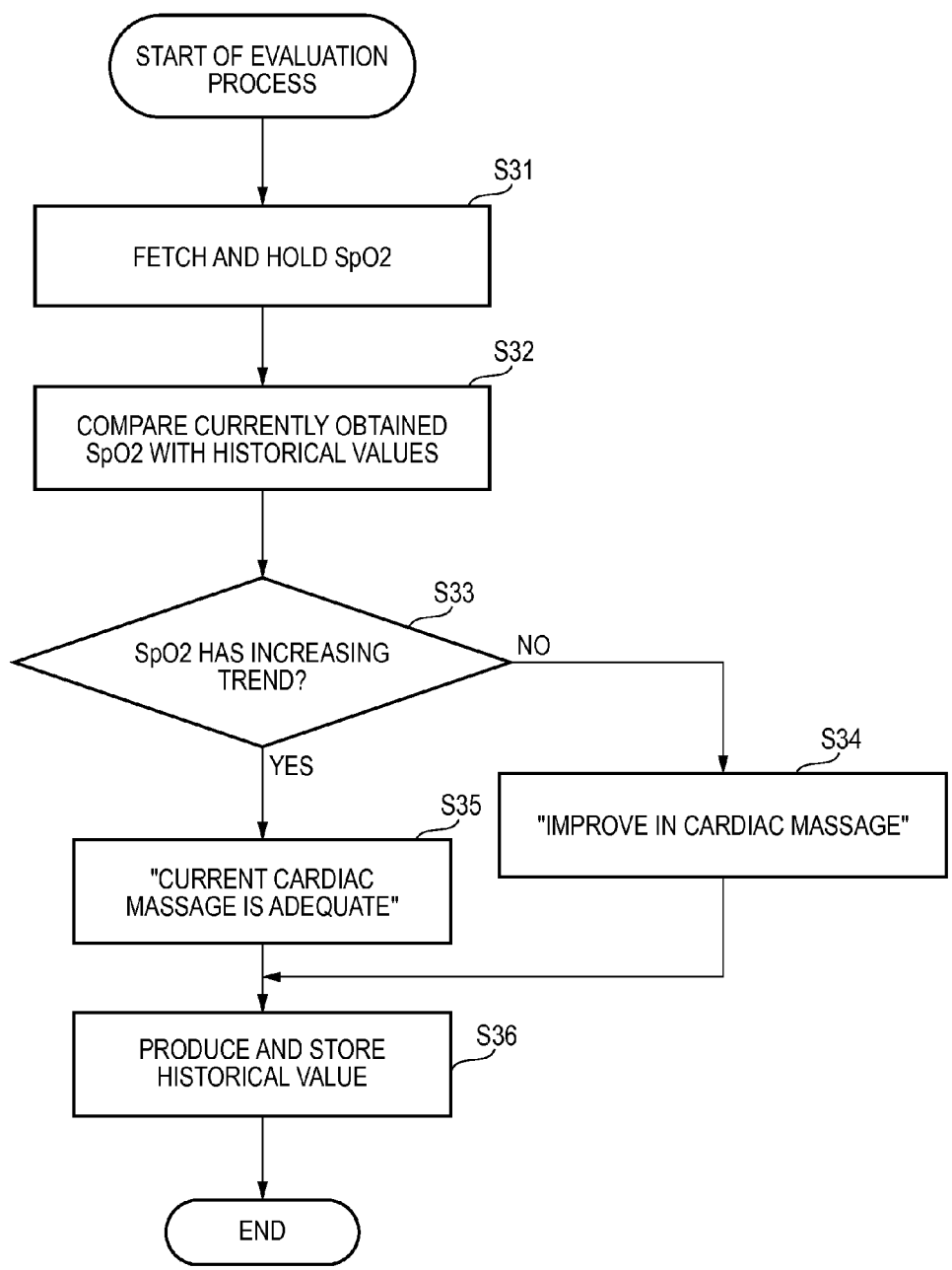
FIG. 6 is a flowchart illustrating the operation of the second embodiment of the cardiopulmonary resuscitation monitoring apparatus of the invention.

The evaluating unit 30A operates based on the flowcharts of FIGS. 5 and 6. Therefore, the operation will be described with reference to the flowcharts. By using the output of the detecting unit 10, the evaluating unit 30A obtains information indicating whether cardiopulmonary resuscitation is being executing or not (S21), and detects whether cardiopulmonary resuscitation is being executing or not (S22). If being executed, the evaluation process by the evaluating unit 30A is activated (S23), and, if not being executed, the evaluation process by the evaluating unit 30A is stopped (S24).

FIG. 6 is the flowchart of the evaluation process by the evaluating unit 30A. The evaluating unit 30A fetches and holds the oxygen saturation signal SpO2 which is the output of the pulse oximeter 20, in synchronization with chest compression in cardiopulmonary resuscitation (S31), compares the oxygen saturation signal SpO2 which is fetched and held, with past historical values (S32), and detects whether the blood oxygen saturation has an increasing trend or not (S33).

If it is determined in step S33 that the blood oxygen saturation does not have an increasing trend, the message information of "Improve in cardiac massage" is sent to the displaying device 40 which is an outputting unit, to be displayed thereon (S34). If it is determined in step S33 that the blood oxygen saturation has an increasing trend, the message information of "Current cardiac massage is adequate" is sent to the displaying device 40 which is an outputting unit, to be displayed thereon (S35). In succession to step S34 or S35, a historical value is produced by using the current blood oxygen saturation, and stored (S36). Then, the process is ended.

According to an aspect of the invention, the detection signal of the timing of chest compression during execution of cardiopulmonary resuscitation is obtained, and evaluation related to cardiopulmonary resuscitation is performed based on the oxygen saturation which is detected by the pulse oximeter at the chest compression timing that is based on the obtained detection signal. Therefore, the blood is moved by the chest compression, and this is captured as a pulse wave, thereby enabling the pulse oximeter to perform an SpO2 measurement. From the measurement output of the pulse oximeter, the trend of blood oxygenation is measured, and a cardiac massage maneuver by a rescuer or the like can be guided so as to be properly performed.

It is often that the patient who is undergoing cardiac massage has no cardiac pulsation. Therefore, a related-art pulse oximeter cannot measure the oxygen saturation (SpO2). According to an aspect of the invention, however, the timing of chest compression which is detected by the detecting unit is assumed as cardiac pulsation, and synchronization with the timing is performed, and, even in an environment where the oxygen saturation (SpO2) cannot be measured by the related-art technique, measurement of the oxygen saturation (SpO2) is therefore enabled.

According to an aspect of the invention, the detecting unit is disposed, and hence noises (for example, a body motion and vibrations in an ambulance car) which are asynchronous with the chest compression can be removed, so that the oxygen saturation (SpO2) can be accurately measured.

When the oxygen saturation (SpO2) is detected during the chest compression, in the related-art technique, the S/N ratio is poor, and accurate measurement cannot be performed. According to an aspect of the invention, the light emitting and receiving sections constitute the detecting unit, and the detecting unit can be placed on the surface of the living body. Consequently, a volume change of the blood layer including both an artery and a vein can be taken out as a large signal. When the oxygen saturation (SpO2) of arterial blood is increased, therefore, also that of venous blood is increased. Even when only the arterial oxygen saturation is not selectively extracted unlike the related art, therefore, it is possible to determine whether the cardiac massage maneuver is effective or not.

What is claimed is:

1. A cardiopulmonary resuscitation monitoring apparatus comprising:
   a detecting unit configured to obtain a timing of a chest compression period from a detection signal during execution of cardiopulmonary resuscitation;
   a pulse oximeter configured to detect a change of a blood volume over the chest compression period based on the timing, and configured to obtain an oxygen saturation from the change of the blood volume;
   an evaluating unit configured to perform evaluation related to the cardiopulmonary resuscitation based on the oxygen saturation; and
   an outputting unit configured to perform an outputting operation in accordance with a result of the evaluation.

2. The cardiopulmonary resuscitation monitoring apparatus according to claim 1, wherein the detecting unit comprises a displacement sensor, a speed sensor, an acceleration sensor, or a pressure sensor.

3. The cardiopulmonary resuscitation monitoring apparatus according to claim 1, wherein:
   a light emitting section and a light receiving section of the pulse oximeter constitute the detecting unit; and
   the detecting unit is adapted to be placed on a surface of a living body.

4. The cardiopulmonary resuscitation monitoring apparatus according to claim 1, wherein the detecting unit notifies the timing of chest compression period to the pulse oximeter.

* * * * *